(12) United States Patent
Swartz et al.

(10) Patent No.: US 6,200,331 B1
(45) Date of Patent: Mar. 13, 2001

(54) ELECTROCONVULSIVE THERAPY TESTING AND TRAINING DEVICE

(75) Inventors: Conrad Melton Swartz, Richmond Heights, MO (US); Richard Stephen Abrams, Chicago, IL (US)

(73) Assignee: Somatics, Inc., Lake Bluff, IL (US)

( * ) Notice: Subject to any disclaimer, the term of this patent is extended or adjusted under 35 U.S.C. 154(b) by 0 days.

(21) Appl. No.: 09/378,817

(22) Filed: Aug. 23, 1999

(51) Int. Cl.[7] ................................................ A61N 1/00
(52) U.S. Cl. ............................................................ 607/1
(58) Field of Search .................... 607/1, 2, 45; 600/509, 600/544, 545, 546

(56) References Cited
U.S. PATENT DOCUMENTS 5,836,993 * 11/1998 Cole ........................................ 607/2

* cited by examiner

Primary Examiner—Scott M. Getzon
(74) Attorney, Agent, or Firm—Eliot S. Gerber

(57) ABSTRACT

A free-standing device for the testing of ECT (electroconvulsive therapy) instruments, and for training doctors in using such instruments, includes circuits to generate electrical wave forms which simulate the EEG (electroencephalograph) detectable brain waves, EMG (electromyograph) muscle activity and heart beats of a patient undergoing ECT. In one embodiment the ECT output leads of the ECT instrument are plugged into the device, the training doctor selects the ECT current and the device generates response EEG and EMG waveforms. It also measures the current and displays its measurement as a test of the accuracy of the stimulus selection controls of the ECT instrument.

20 Claims, 1 Drawing Sheet

ELECTROCONVULSIVE THERAPY TESTING AND TRAINING DEVICE

FIELD OF THE INVENTION

The present invention relates to medical devices and more particularly to devices for the testing of ECT (electroconvulsive therapy) instruments and for training in the usage of such instruments.

BACKGROUND OF THE INVENTION

The present invention relates to an ECTOBRAIN (TM of Somatics, Inc.) dual function device. It is a computer controlled device that simulates a patient undergoing ECT. It can be used for two separate but related purposes, namely:

(1) To train psychiatrists in the correct use of ECT devices, including the accurate interpretation of the printed and auditory output of ECT devices;

(2) To test the integrity, calibration and functioning of ECT devices used to administer electroconvulsive therapy (ECT).

Training Function

Over the past 60 years modern ECT (electroconvulsive therapy) has evolved into a highly sophisticated procedure conducted under general anesthesia (Abrams, 1997). Successful ECT requires the treating psychiatrist to have intimate knowledge of the several parameters of the electrical stimulus, as well as the ability to monitor and interpret the electroencephalogram (EEG), electrocardiogram (ECG), and electromyogram (EMG) records now routinely obtained during each ECT treatment. For example, U.S. Pat. Nos. 4,878,498 and 5,260,302: Electroconvulsive Therapy Apparatus and Method for Automatic Monitoring of Patient Seizures; and U.S. Pat. No. 5,871,517: Convulsive Therapy Apparatus to Stimulate and Monitor the Extent of Therapeutic Value of the Treatment, describe ECT instruments which monitor one or more of EEG, ECG and EMG. The American Psychiatric Association Task Force Report (1990) recommends monitoring of EEG and ECG during ECT.

These above-named patents and articles and other patents and articles mentioned herein are incorporated by reference.

Specific training and skill in the administration of modern ECT is required for hospital accreditation and for board-certification in psychiatry. However, many hospitals and psychiatric residency training programs lack either sufficient trained personnel to instruct psychiatric residents and staff to the requisite level of skill, or lack a sufficient number of patients receiving ECT to provide the necessary clinical experience. In a survey of ECT usage in New York hospitals, Asnis et al (1976) concluded that "training programs were minimal and unplanned." Pippard (1992), following up on the results of an earlier, highly-critical survey of the quality of ECT administration in the United Kingdom (Pippard and Ellam 1981), found that despite the specific recommendations of their 1981 study "stimulus-dosing is [still] usually by habit rather than rational strategy, and routine instrument settings differ fourfold between clinics." An Australian ECT training survey (Halliday and Johnson, 1995) found that "in most centres, training typically consists of registrars [psychiatric residents] being supervised once or twice by another registrar, and thereafter administering ECT alone."

This world-wide deficiency in ECT training has led several medical educational centers (e.g., Columbia University, Duke University, Long Island Jewish-Hillside Hospital Medical Center) to establish continuous, year-round ECT workshops for the purpose of training psychiatrists in ECT. These workshops last from 1 to 5 days and provide a range of didactic and clinical experience in various aspects of ECT.

Although such extramural training programs are important, they are too few to make up for the inadequate training in ECT received by hundreds of psychiatric residents graduated each year from U.S. medical schools and hospitals. Moreover, even these specialized ECT courses may lack sufficient patients receiving ECT to provide each trainee with "hands-on" experience in administering the treatment and interpreting the monitored recordings obtained. No medical educational center possesses all of the various available ECT devices required to train doctors in the use of any ECT device they might reasonably expect to encounter in clinical practice.

ECT Device Testing Function

The electronically sophisticated circuitry used by modern ECT devices to generate therapeutic electrical stimuli, and to monitor and display the physiological functions of interest (EEG, ECG, EMG) is necessarily sensitive—requiring frequent calibration—and subject to occasional malfunction. When such a malfunction occurs, patients may suffer from not being able to receive their scheduled ECT treatment, due to the time and effort required for a biomedical analysis of the problem. Such problems often require that the malfunctioning ECT device be returned to the manufacturer for testing and repair. When such return is required, the hospital incurs the cost of renting a "loaner" device to temporarily replace the malfunctioning one, the cost of evaluation or repair, and the shipping costs. Alternatively, the hospital incurs the cost of having the manufacturer send a technician to examine the ECT device on site. Moreover, the experience of one ECT device manufacturer (Somatics, Inc., Lake Bluff, Ill.) is that a substantial number of allegedly malfunctioning ECT devices returned for testing actually have nothing wrong with them—operator error is determined to be the problem.

SUMMARY OF THE INVENTION

In accordance with the present invention there is provided a device called ECTOBRAIN (TM of Somatics, Inc.) which may perform either one, or two, functions. One function is to test ECT instruments by generating a sequence of electrical outputs that simulate the EEG, EKG and EMG of various types of patients. That set of generated electrical stimuli is a standard set of data. That standard data set is compared with the responses of the ECT instrument to the simulated data generated by the ECTOBRAIN. If the responses of the ECT instrument are outside of pre-set limits, the instrument is considered to be malfunctioning and should be re-calibrated or repaired.

One embodiment of the present invention is a metal box ("ECTOBRAIN") containing battery-powered electronic components (e.g., microprocessor, resistors, printed circuit board, analog-to-digital converter, externally programmed chips). It generates three different electrical wave-forms which simulate the waveforms of a patient, namely, an EEG wave-form, an ECG wave-form, and an EMG wave-form. These wave-forms have been derived from FM (analog) tape recordings of EEG, ECG and EMG in actual patients undergoing ECT. One or more 30-second segments of the analog recordings are de-artifacted, digitized, and stored on chips, or other digital storage devices, to provide a complete service "continuous-loop" repetitive output function. The surface of the box contains separate connectors, e.g., banana-plug receptacles, for attaching the ECT stimulus leads of an ECT device, and for attaching the EEG, ECG and EMG recording leads of an ECT device, e.g., post connectors.

With the ECTOBRAIN powered on, the ECT stimulus and recording cables are connected to their respective receptacles, and the ECT device is powered on. The ECTO-BRAIN then provides a set of wave forms which are a complete simulation of a patient, as follows:

1. Initiating the impedance testing function of the ECTOBRAIN by applying an impedance-testing current to connect a resistance within the ECTOBRAIN, for example, 200 ohms impedance. That resistance causes an impedance test value to be displayed on the ECT device, which should be, for example, 200 ohms, with a range of ±20 ohms. In another embodiment, this resistance value can be varied by the operator (usually the instructor), for training purposes, to produce a number that is too high, too low, or in the correct range.

2. Pressing the TREAT (stimulus) button of an ECT device automatically initiates its chart recorder. The ECTOBRAIN generates a continuous-loop signal of each of the three wave-forms (EEG, ECG, EMG), which appear as tracings on the paper record of the chart recorder according to the number and type of channels selected on the ECT device. For example, if the ECT device has 4 channels—for displaying 2 channels of EEG and 1 channel each of ECG and EMG—and those 4 channel leads are connected to the corresponding receptacles of the ECTOBRAIN, the paper record will display 2 channels of EEG and 1 channel each of ECG and EMG, just as would occur with a live patient. If an ECT device with a 2-channel chart recorder (e.g., for EEG and ECG) is connected to the corresponding ECTOBRAIN receptacles, the paper record will display 1 channel of EEG and 1 channel of ECG.

3. Simulated EEG, ECG and EMG signals are generated by the ECTOBRAIN which mimic the typical progression of an ECT-induced seizure, observed during an actual ECT treatment, as described in Abrams (1997):
   a. The EEG exhibits three phases, early-mid-, and post-ictal, with the typical wave-form patterns corresponding to each phase.
   b. The ECG shows a normal rate prior to stimulus onset, then a rapid rate during the EEG seizure, followed by a return to normal rate when the EEG seizure reaches the post-ictal phase.
   c. The EMG is non-reactive prior to stimulus onset, becomes markedly active during the early- and mid-ictal EEG phases, and terminates several seconds prior to the termination of the EEG seizure in the post-ictal phase.

In the training embodiment, and also optionally in the testing embodiment, the operator can vary the quality of the EEG pattern to reflect a therapeutically inadequate seizure (e.g., insufficient amplitude or duration, absence of spike phase), and can vary the ECG pattern to show potentially dangerous patterns of cardiac response (e.g., ventricular tachycardia or fibrillation).

In ECT devices that provide an audible as well as a written representation of the EEG signal (see U.S. Pat. No. 4,777, 952: Device and Method for obtaining an Audible Indication of EEG in Conjunction with Electroconvulsive Therapy), this audible signal is automatically generated by the ECT device when its TREAT (stimulus) switch is pressed while the stimulus leads are connected to the ECTOBRAIN. This permits the instructor to train the students in the interpretation of the resulting "audible EEG."

In addition to the patient simulation functions, the ECTOBRAIN contains circuitry and programs for testing the electrical stimulus dose output of an ECT device via digital analysis of the ECT stimulus transmitted from the ECT device to the ECTOBRAIN via the ECT stimulus cable.

At the time of passage of the ECT stimulus, which is a brief-pulse, square wave stimulus in the range of 0.1 to 8 seconds duration, the ECTOBRAIN performs a pulse-by-pulse digital analysis of the stimulus and computes the total stimulus charge. In one embodiment, which displays the ECT stimulus, the operator can compare the actual charge output value with the charge value selected by the operator prior to initiating the stimulus. If they are not the same, for example, within 1–3%, then there may be a problem with the ECT device, e.g., the stimulus selected is not being generated by the ECT device or the measurement made of the stimulus by the ECT device is incorrect. In either case, the ECT device should be repaired.

This comparison may provide a test of the safety and accuracy of the dosage output of the ECT device. It tests the accuracy of two important portions of the ECT device, namely, (i) is the ECT stimulus generated by the ECT device within a selected range of the quantity of stimulus which the operator has chosen, and (ii) is the dosage output which is recorded by the ECT device within a selected range of the actual dosage output of the device. The ECTOBRAIN has indicators to show if the dose set by the operator is within a predetermined limit of the dose generated by the ECT device. A green light is lit if the dose is within the limit and a red light is lit if the dose is below or above that limit. When examined together with the printout of the other ECT stimulus parameters printed by the ECT device, and with the appearance of the EEG, ECG, and EMG tracings on the paper chart, the dosage output figure provides a complete and definitive test of the functioning of an ECT device.

If a malfunction of the ECT device is suspected, examination by the manufacturer (or by a member of the hospital's biomedical engineering department, if it has one) of the recording strip with its tracings, and written report, may provide the necessary information to determine the existence and nature of the suspected malfunction. The reviewer can determine whether it is device-related or due to operator error. This may avoid the need to ship the device back to the manufacturer for testing, or for the manufacturer to send a technician to the hospital to examine the ECT device on site.

This is especially useful in geographically isolated or rural areas where hospitals may not have biomedical engineering departments, and where the distances between the hospital and the distributor's offices may be hundreds or even thousands of miles.

BRIEF DESCRIPTION OF THE DRAWINGS

In the accompanying drawing, the figures show the inventors' presently known best mode of practicing the invention. In the drawing.

DETAILED DESCRIPTION OF THE INVENTION

Figure 1:
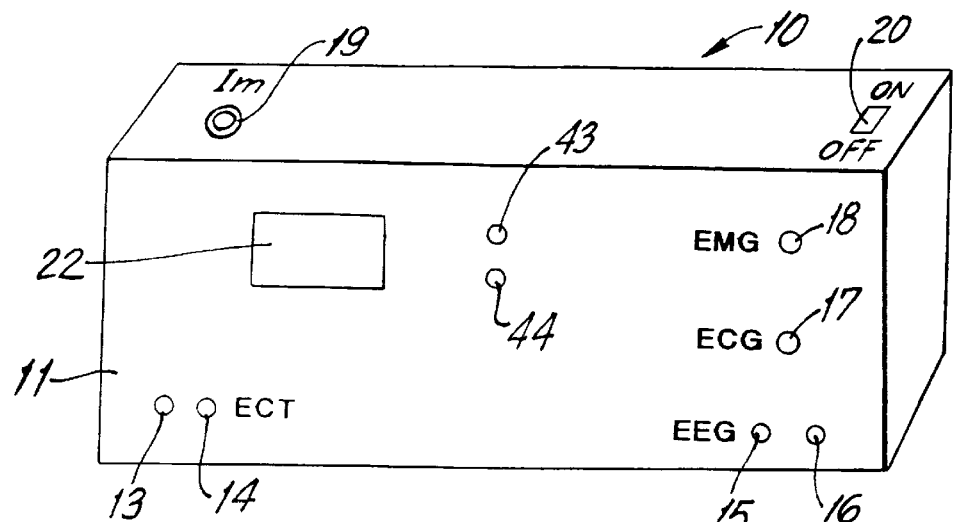
FIG. 1 is a perspective view of the test and training device of the present invention.

As shown in FIG. 1, the ECTOBRAIN device 10 (TM of Somatics, Inc.) comprises a metal box casing 11. The casing 11 encloses a rechargeable battery, or other power source, a microprocessor, printed circuit board, A/D converter (analog-digital) and a memory chip (integrated circuit) which is programmed by suitable software.

An impedance testing switch 12, labeled IM, is located on the casing 11. A series of banana plug sockets (female) 13–18 are also located on casing 11. The sockets 13,14 are for ECT, the sockets 15,16 are for EEG, the socket 17 is for ECG and the socket 18 is for EMG.

A switch 19, labeled IM, is for testing the impedance of the leads. When the switch 19 is operated, the circuitry generates a programmed sequence of voltages at each of the leads 13–18 which simulate a typical and acceptable impedance, for example, 100 ohms.

In the embodiment, which is only a testing device without a training function, the entire program may be automatic after operation of the on-off switch 20.

In the testing mode, to test the detecting circuits of the ECT, without testing of its stimulus and without training, the device 10 will automatically generate electrical signals to test the ECT device. An example of such signals is as follows:

1. This test is without connection of the ECT device to the sockets 13,14 of the ECTOBRAIN device 10. EEG leads connected to sockets 15,16 receive a programmed sequence of wave forms which simulate a typical patient's EEG responses during ECT treatment. The EEG wave forms generated by device 10 are analog signals in the microvolt range which simulate the EEG wave forms of a patient. The EEG simulated wave forms are analyzed, automatically, by the ECT device which produces a paper record of the results and a paper record of the analog signal as wavy lines.

The ECT device receives the electrical signal outputs as analog signals and (i) converts the analog signals into digital data to produce its analysis, which is printed, and (ii) amplifies the raw analog EEG wave forms and prints them as wavy lines.

The operator is instructed to compare the ECT device's results with the standard wave forms generated by the ECTOBRAIN device 10. For example, the device 10 will generate the following simulated EEG reference value (standard) wave forms derived from ECT treatment of one, or more, typical patients:

(i) intense ECT seizure with high amplitude EEG and strong postictal EEG suppression;

(ii) insufficient ECT seizure with low amplitude EEG and without postictal EEG suppression.

One type of ECT device, called the Thymatron DGx (TM of Somatics, Inc.), will produce a paper strip showing in digital format, generally percentage, a list of various indicia, such as "postictal suppression index", "seizure energy index" and "seizure concordance index." The wave-forms generated by the ECTOBRAIN device 10 are programmed to produce a standard set of such indicia on the Thymatron™, and/or other, ECT devices. For example, the device 10 is programmed to generate a postictal suppression index of 91%. The receiving ECT device should show a result within a pre-set range, for example, ±5%, i.e., an acceptance range of 86% to 96%. The timing is also tested, i.e., the EEG endpoint at 40 seconds, which should result in a showing by the ECT device of an EEG endpoint in the range of 38–42 seconds.

As another example, the "seizure energy index" is an integration of the EEG voltage across the entire seizure. The EEG simulated voltage is first set to a standard simulating a strong seizure. In one example, the ECT device should indicate a seizure energy index of 1700±50. Then the ECTOBRAIN simulates a weak seizure and that standard seizure energy index should be, for example, at 300±20.

Other examples of EEG indicia which may be recorded by the TM Thymatron™, or other ECT devices, and which may be generated under program control by the ECTOBRAIN, include the following:

1. "EEG area"—the area under the curve of the absolute EEG voltage, see U.S. Pat. No. 5,871,517 at column 3, lines 40–60. The measurement may be over the entire band 2 to 49 Hz or any range of frequencies within that band.
2. "EEG area rate"—the EEG area per unit time
3. times of occurrence of the EEG area rate maxima and minima.
4. maximum positive EEG amplitude
5. maximum absolute EEG amplitude
6. "absolute power"—the mean integrated voltage in selected bands over the duration of the ECT-induced seizure. The preferred bands of interest are Delta (2–3.5 Hz), Theta (3.5–7.5 Hz), Alpha (7.5–12.5 Hz), and lower Beta (12.5–25 HZ).
7. Seizure Coherence—taken over the entire band 2–25 Hz or/and at Delta, Theta, Alpha, lower Beta. For example, coherence may be voltage differences from mirror image electrodes subtracted from mean voltage. Alternatively, differences between electrodes on the left side of the head are subtracted from differences between electrodes on the right side of the head.

2. The ECTOBRAIN device generates an analog signal at the millivolt level simulating a patient's heart activity at ECG socket 17. The first simulation is of an intense EEG seizure and shows a heart beat rate of 150 beats per minute and an abrupt slowing of rate corresponding to the end of motor seizure activity (about twice an average patient's heart beat rate pre-ECT). The second simulation is of an insufficient ECT seizure and a heart beat rate of 120 (about 10% above that of a normal patient pre-ECT).

3. The ECTOBRAIN device generates a millivolt level analog signal to EMG socket 18 which simulates the patient's muscle activity during ECT. First, an intense seizure is simulated. The simulated EMG signal is of a long tonus EMG phase, and an EMG endpoint. Secondly, an insufficient seizure is simulated by lower level EMG signals.

The Thymatron™ ECT device produces a paper strip showing wavy lines representing the patient's EEG and EMG. The ECTOBRAIN™ device 10 generates voltage wave-forms which simulate the patient's EEG and EMG and may also generate test wave forms. A suitable test wave form is a sine wave. In all cases, the paper strip may be visually compared with a standard test strip. For example, the standard test strip may show wavy lines, and a sine curve is printed on clear plastic so that it may be overlaid and compared with the ECT's device paper strip produced in response to the test.

Figure 2:
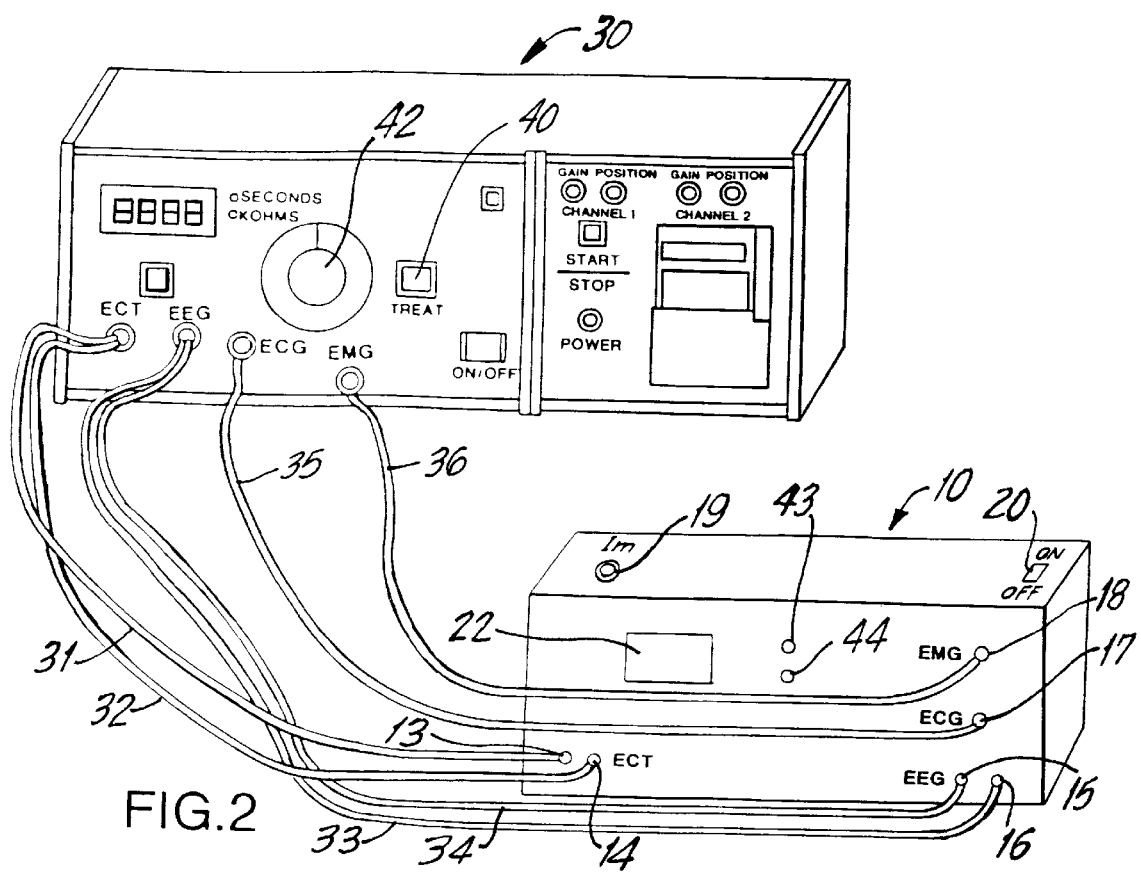
FIG. 2 is a perspective view of the device of FIG. 1 connected to an ECT stimulus device.

To test the electrical stimulus dose generated by the ECT device 30, its ECT leads 31 and 32 are connected into ECT sockets 13,14 of the test device 10 (FIG. 2). The dial 42 of the ECT device 30 is operated to select the ECT stimulus dose and the TREAT button 40 is operated. The test device 10 receives the stimulus current and measures it. The test device has green indicator light 43 which lights up if the ECT stimulus dose is within an acceptable range. If the stimulus dose is outside of the acceptable range, the red light 44 is lighted. In addition, an option is to display the measurement on a display screen 22, preferably a small LCD screen. The preferred measurements for the dose charge are milliCoulombs (mC) and Joules—preferably both being shown.

In addition to the testing of an ECT device, the ECTOBRAIN™ device 10 may be used as an aid in the training of ECT practice. For this purpose the ECT device 30 is connected to the test device 31.

As shown in FIG. 2, the ECT leads 31,32 of ECT device 30 are connected into sockets 13,14; the EEG leads 33,34 are connected into sockets 15,16; the ECG lead 35 is connected into socket 17; and the EMG lead 36 is connected into socket 18.

The trainee will be presented with data regarding a hypothetical ECT patient, including the patient's age, gender, concurrent medications, electrode placement and the number of ECT treatments the patient has received over the preceding month.

The trainee, for example, a psychiatric resident, will then determine what he believes is the correct ECT dosage. For example, the resident may decide that the dosage should be bilateral ECT should be 176 mC at 50 Hz frequency and a pulsewidth of 1.0 m secs. for a duration of 2 seconds.

The test device 10 is programmed to produce, on a random basis, a number of responses to that stimuli. One response would be a typical patient who attains a strong seizure.

Another programmed response is a weak seizure. The resident-trainee would then be able to look at the data produced by the ECT device 30 and review whether the dosage he selected was appropriate and effective.

In the case of the training device the EEG, EMG and ECG simulations that are the output of the device 10 are responsive to the electricity (stimulus) delivered to the ECT input sockets. The characteristics of the stimulus charge include its pulse width, current, charge rate, frequency, or any combination of these characteristics. The trainee derives these characteristics from a calculation based on the simulated patient, which can include such factors as age, gender, concurrent medications, electrode placement, and the number of ECT treatments the patient received over the preceding period, i.e., a month.

The following are some examples to illustrate the dependence of the simulation of EEG, ECG, and EMG on the electrical measurements and the stimulus characteristics. With a high electrical stimulus charge, the EEG, EMG, and ECG simulations would describe an intense seizure. This would typically include a high amplitude EEG, strong postictal EEG suppression, a long tonus EMG phase, an EMG endpoint near the end of high frequency activity on the EEG, a heart rate peak about twice baseline, and an abrupt slowing of heart rate shortly after the end of motoric seizure activity. With a medium dosage stimulus charge they would simulate an average seizure. With a low stimulus charge, the measurements would describe a seizure of poor quality. With a very low stimulus charge (much below a reference stimulus), they would show no sign of seizure.

The computer programs will present simulations of clinical situations. For example, patients will present information to the trainee who will use the combination of ECT device 30 and test device 10. These programs may operate in a manner that is contingent on selection of dosage by the trainee to simulate clinical situations or test the trainee's knowledge and skill in conjunction with the operation of the device.

Modifications may be made in the invention within the scope of the subjoined claims. For example, the training device 10 may be a "phantom" in the form of a model of a patient's head. The ECT leads would be connected to electrodes which would be applied to the model head. The model head, at positions corresponding to the locations at which the electrodes are applied, would have receiving electrodes and circuitry with an impedance typical of the impedance of a patient.

REFERENCES

Asnis G M, Fink M, Saferstein S (1978): ECT in metropolitan New York hospitals: a survey of practice. *Am J Psychiatry* 135:479–82

Pippard J, Ellam L (1981): Electroconvulsion treatment in Great Britain 1980. *Lancet* 2:1160–1161

Pippard J (1992): Audit of electroconvulsive treatment in two national health service regions. *Br J Psychiatry* 160:621–37

Halliday G, Johnson G (1995): Training to administer electroconvulsive therapy: a survey of attitudes and experiences. *Aust N Z J Psychiatry* 29:133–138

What is claimed is:

1. A testing device to test the functioning of an ECT (electroconvulsive therapy) instrument; the ECT instrument performing EEG (electroencephalograph) and EMG (electromyograph) analysis, the testing device comprising:

(a) a casing, and within the casing;
   (b) at least one EEG connector adapted to receive an EEG lead from the ECT instrument, EEG circuit means connected to the EEG connector to generate electrical wave forms that simulate the brain waves of a patient undergoing ECT in order to test the EEG analysis of the ECT instrument;
   (c) at least one EMG connector adapted to receive an EMG from the ECT instrument, EMG circuit means connected to the EMG connector to generate electrical wave forms that simulate the muscle activity of a patient undergoing ECT in order to test the EMG analysis of the ECT instrument.

2. A testing device as in claim 1 wherein the ECT instrument performs ECG (electrocardiograph) analysis and the testing device, within the casing, further comprises at least one connector adapted to receive an ECG lead from the ECT instrument, and ECG circuit means to generate electrical wave forms that simulate the heart activity of a patient undergoing ECT in order to test the ECG analysis of the ECT instrument.

3. A testing device as in claim 2 wherein the ECG circuit means generates electrical wave forms that simulate the heart beats of a patient.

4. A testing device as in claim 1 wherein the ECT instrument has two EEG leads and the testing device in (b) has two EEG connectors.

5. A testing device as in claim 1 wherein the ECT instrument displays a patient's brain waves in the form of a wavy and spikey line and in (b) the EEG circuit means generates a wave form to be displayed by the ECT instrument as a wavy and spikey line.

6. A testing instrument as in claim 1 wherein the ECT instrument computes one or more EEG measures from the group, including: EEG area rate, EEG area, times of occurrence of EEG area rate maxima and minimia, maximum positive EEG amplitude, maximum absolute EEG amplitude, absolute power seizure coherence, seizure energy index, postictal suppression index, seizure energy index, seizure concordance index; and the EEG circuit means of (b) generates electrical wave forms which are a predetermined standard of one or more of said EEG measures.

7. A testing and training device to test the functioning of an ECT (electroconvulsive therapy) instrument and to train operators of the instrument; the ECT instrument performing EEG (electroencephalograph) and EMG (electromyograph) analysis and generating ECT voltages in response to ECT selection by an operator, the device comprising:

(a) a casing, and within the casing;
(b) at least one EEG connector adapted to receive an EEG lead from the ECT instrument, EEG circuit means connected to the EEG connector to generate electrical wave forms that simulate the brain waves of a patient undergoing ECT;
(c) at least one EMG connector adapted to receive an EMG from the ECT instrument, EMG circuit means connected to the EMG connector to generate electrical wave forms that simulate the muscle activity of a patient undergoing ECT;
(d) at least one input ECT connector adapted to receive an ECT lead from the ECT instrument, measurement circuit means connected to the ECT connector to measure the electrical current at the ECT connector; and
(e) display means to display the measurement of (d).

8. A device as in claim 7 wherein the ECT instrument performs ECG (electrocardiograph) analysis and the device, within the casing, further comprises at least one connector adapted to receive an ECG lead from the ECT instrument, and ECG circuit means to generate electrical wave forms that simulate the heart activity of a patient undergoing ECT in order to test the ECG analysis of the ECT instrument.

9. A testing device as in claim 8 wherein the ECG circuit means generates electrical wave forms that simulate the heart beats of a patient.

10. A device as in claim 7 wherein the display means comprises a visual display panel on the casing.

11. A testing device as in claim 7 wherein the ECT instrument has two EEG leads and the testing device in (b) has two EEG connectors.

12. A testing device as in claim 7 wherein the ECT instrument displays the patient's brain waves in the form of a wavy and spikey line and in (b) the EEG circuit means generates a wave form to be displayed by the ECT instrument as a wavy and spikey line.

13. A testing instrument as in claim 7 wherein the ECT instrument computes one or more EEG measures from the group, including: EEG area rate, EEG area, times of occurrence of EEG area rate maxima and minima, maximum positive EEG amplitude, maximum absolute EEG amplitude, absolute power, seizure coherence, seizure energy index, postictal suppression index, seizure energy index, seizure concordance index; integrated absolute value of voltage and coherence, and the EEG circuit means of (b) generates electrical wave forms which are a predetermined standard of one or more of said EEG measures.

14. A testing and training device to test the functioning of an ECT (electroconvulsive therapy) instrument to train operators of the instrument performing EEG (electroencephalograph) and EMG (electromyograph) analysis and generating ECT voltages in response to ECT selection by an operator, the device comprising:

(a) casing, and within the casing;
(b) at least one EEG connector adapted to receive an EEG lead from the ECT instrument, EEG circuit means connected to the EEG connector to generate electrical wave forms that simulate the brain waves of a patient undergoing ECT;
(c) at least one EMG connector adapted to receive an EMG from the ECT instrument, EMG circuit means connected to the EMG connector to generate electrical wave forms that simulate the muscle activity of a patient undergoing ECT;
(d) at least one input ECT connector adapted to receive ECT current from the ECT instrument; and
(e) a computer based control circuit means to control the generation of wave forms of (b) and (c) in response to receipt of ECT current from the ECT instrument, the control circuit means simulating a normal patient's EEG and EMG detected activity during
  (i) an intense seizure in response to a high ECT stimulus (as would be seen with a stimulus over 2.0 times average seizure threshold for ECT), and
  (ii) an average seizure in response to a normal ECT stimulus (near seizure threshold for ECT).

15. A device as in claim 14 and in (e) the control circuit means also simulating (iii) a lack of seizure in response to a below normal ECT stimulus (below seizure threshold for ECT).

16. A device as in claim 15 wherein the ECG circuit means generates electrical wave forms that simulate the heart beats of a patient.

17. A device as in claim 15 wherein the ECT instrument has two EEG leads and the device in (b) has two EEG connectors.

18. A device as in claim 15 wherein the ECT instrument displays a patient's brain waves in the form of a wavy line and in (b) the EEG circuit means generates a wave form to be displayed by the ECT instrument as a wavy line.

19. An instrument as in claim 15 wherein the ECT instrument processes received EEG by integration and/or conversion to digital data and computing therefrom one or more EEG measures, including area rate, integrated absolute value of voltage and coherence, and the EEG circuit means of (b) generates electrical wave forms which are a series of predetermined standard of one or more EEG measures including integrated absolute value of the voltage, area rate and coherence.

20. A device as in claim 14 wherein the ECT instrument performs ECG (electrocardiograph) analysis and the device, within the casing, further comprises at least one connector adapted to receive an ECG lead from the ECT instrument, and ECG circuit means to generate electrical wave forms that simulate the heart activity of a patient undergoing ECT.

* * * * *